United States Patent
Frodl

(10) Patent No.: US 7,332,719 B2
(45) Date of Patent: Feb. 19, 2008

(54) GAS SENSOR ARRANGEMENT WITH IMPROVED LONG TERM STABILITY AND MEASURING METHOD

(75) Inventor: Robert Frodl, München (DE)

(73) Assignee: Tyco Electronics Raychem GmbH, Ottobrunn (DE)

( * ) Notice: Subject to any disclaimer, the term of this patent is extended or adjusted under 35 U.S.C. 154(b) by 0 days.

(21) Appl. No.: 11/380,787

(22) Filed: Apr. 28, 2006

(65) Prior Publication Data

US 2006/0249681 A1    Nov. 9, 2006

(30) Foreign Application Priority Data

May 4, 2005    (DE)    ........... 10 2005 020 864

(51) Int. Cl.
*G01F 5/02*    (2006.01)
(52) U.S. Cl. .................................................. 250/343
(58) Field of Classification Search ................. 250/343
See application file for complete search history.

(56) References Cited

U.S. PATENT DOCUMENTS

| | | | |
|---|---|---|---|
| 4,346,296 A | | 8/1982 | Passaro et al. |
| 5,448,071 A | * | 9/1995 | McCaul et al. ............. 250/343 |
| 5,905,270 A | | 5/1999 | McCaughey et al. |
| 6,469,303 B1 | * | 10/2002 | Sun et al. .................... 250/343 |
| 2005/0151082 A1 | | 7/2005 | Coffin et al. |
| 2005/0285055 A1 | | 12/2005 | DelFavero et al. |

FOREIGN PATENT DOCUMENTS

| | | |
|---|---|---|
| DE | 19925196 A1 | 5/1999 |
| EP | 0 616 207 A2 | 9/2004 |
| JP | 8-334409 | 12/1996 |
| JP | 10-318922 | 12/1998 |
| JP | 2000-215990 | 8/2000 |
| WO | 00/55603 A1 | 9/2000 |

* cited by examiner

*Primary Examiner*—Dave Porta
*Assistant Examiner*—Jessica L Eley
(74) *Attorney, Agent, or Firm*—Barley Snyder LLC

(57) ABSTRACT

The present invention relates to a gas sensor arrangement comprising at least one radiation source emitting radiation, a gas measuring chamber which may be filled with a gaseous analyte containing at least one analyte to be measured, and comprising at least one detector device which detects the radiation and generates an output signal indicating the presence and/or the concentration of the analyte. In order to provide an improved gas sensor arrangement of the type mentioned at the outset which ensures, in a particularly simple manner, long-term stable operation of the arrangement even over long periods of time, the control device comprises a power detection unit which may be operated to measure the electrical output consumed by the at least one radiation source.

15 Claims, 6 Drawing Sheets

GAS SENSOR ARRANGEMENT WITH IMPROVED LONG TERM STABILITY AND MEASURING METHOD

FIELD OF THE INVENTION

The present invention relates to a gas sensor arrangement comprising at least one radiation source emitting radiation, a gas measuring chamber which may be filled with a gaseous analyte containing at least one analyte to be measured, and at least one detector device which detects the radiation and generates an output signal indicative of the presence and/or the concentration of the analyte. The present invention also relates to an associated measuring method.

BACKGROUND

Gas sensor arrangements of this type are known for detecting a wide range of analytes, for example methane or carbon dioxide. Gas sensors, as described, for example, in EP 0616207 A2, WO 00/55603 A1 or in DE 19925196 C2, are based on the characteristic of many polyatomic gases to absorb radiation, in particular within the infrared wavelength range. In this process, this absorption appears in a wavelength which is characteristic of the relevant gas, for example at 4.24 µm for $CO_2$. Thus, using infrared gas sensors of this type, it is possible to establish the presence of a gas component and/or the concentration of this gas component. Known gas sensors comprise a radiation source, an absorption path, i.e. a measuring chamber and a radiation detector. The radiation intensity measured by the radiation detector is a measurement of the concentration of the absorbent gas.

A broadband radiation source, usually a lamp, is generally used and the wavelength which is of interest is selected via an interference filter or grid. This type of radiation generation is also known as a non-dispersive method and, in the case of infrared-$CO_2$ analysis, is termed the non-dispersive infrared (NDIR) method.

The detection of carbon dioxide is currently becoming increasingly significant in the automotive field. On the one hand, this is due to the fact that the $CO_2$ content of the air inside motor vehicles is monitored in order to increase the energy efficiency for heating and air-conditioning, in order to induce a supply of fresh air via a corresponding fan flap control only when required, i.e. when the concentration of $CO_2$ increases. On the other hand, modem air-conditioning systems are based on $CO_2$ as a coolant. Thus, $CO_2$ gas sensors may perform a monitoring function in connection with $CO_2$ escaping in the event of possible defects.

Particularly in the automotive field, sensors of this type must, however, meet the highest requirements in terms of robustness, reliability and compactness, and long-term stability is required for many years. In this case, the emission of the infrared radiation source must remain stable over the entire service life, or must at least be monitored. However, with the requisite service life of a minimum of ten years and the currently conventional measuring rates of two seconds per measurement, the known IR radiation sources age too intensely to observe the specifications which have to be imposed on an NDIR gas sensor of this type.

Until now, two fundamental approaches have been known to counter this problem. Firstly, it is known to provide at least two beam paths with an infrared radiation source and two detectors, one of the detectors measuring the desired gas and the other measuring the brightness of the lamp with another wavelength. The change in the brightness of the lamp which is detected may be factored into a correction calculation using the second detector.

Another known solution, as described, for example, in DE 19925196 C2, uses at least two beam paths with two infrared sources and only one detector. The first lamp measures at the necessary measuring rate, while the second lamp is used only comparatively rarely for carrying out a comparative measurement. This solution assumes that the ageing of the second lamp is to be disregarded due to the intermittent switching-on.

These known solutions, however, suffer from the problem that on the one hand they are relatively complex and, on the other hand, to assess the lamp radiation they always require the detector signal, which is encumbered with the errors resulting from the long-term drift of the detectors and the parameter fluctuations occurring along the entire measuring path. Furthermore, in the event of an intermittent operation of a reference lamp, the ageing of said lamp can also no longer be disregarded with a service life in the region of ten years.

SUMMARY

An object of the present invention is to provide an improved gas sensor arrangement of the aforementioned type which ensures, in a particularly simple manner, long-term stable operation of the arrangement even over long periods of time.

According to the invention, the gas sensor unit comprises a control device for triggering the radiation source which comprises a power detection unit in order to measure the electrical output consumed by the radiation source. For example, according to the invention, the microcontroller provided in a known manner on an NDIR sensor, which microcontroller determines, during the measurement, the voltage integral of the detector as a measuring signal via an A to D converter, is able to determine the electrical energy in the radiation source circuit which has been converted by the lamp during the measurement. Thus, the consumed electric output and hence the internal resistance of the radiation source and, over time, the working integral of the measuring radiation source may advantageously be determined during the measurement. The measured value may be used in the assessment as a correction factor for normalization to a lamp brightness which prevailed at the time of the initially made calibration in the manufacturing calibration site.

BRIEF DESCRIPTION OF THE DRAWINGS

The present invention will be described in more detail in the following description with reference to the embodiments shown in the accompanying drawings. Similar or corresponding details of the subject-matter according to the invention are denoted by the same reference numerals. In the drawings.

DETAILED DESCRIPTION OF THE EMBODIMENTS

The present invention is based on the idea that during the course of the service life of non-dispersive infrared radiation sources, the internal resistance of the radiation source changes significantly. As could be shown in the course of comprehensive experimental tests, the change in the ageing-induced source brightness in conventional types of operation, i.e. when a lamp is operated either with constant voltage or constant current, is induced by different electric outputs being converted into radiation. With a constant voltage, this output is calculated as $$P = \frac{U^2}{R_L},$$

and with a supply of a constant current, it is calculated as $P = I^2 R_L$. In this calculation, P represents the electric output converted in the radiation source, Q represents the voltage dropping at the source, I represents the current flowing through the source and $R_L$ represents the internal resistance of the source.

Figure 1:
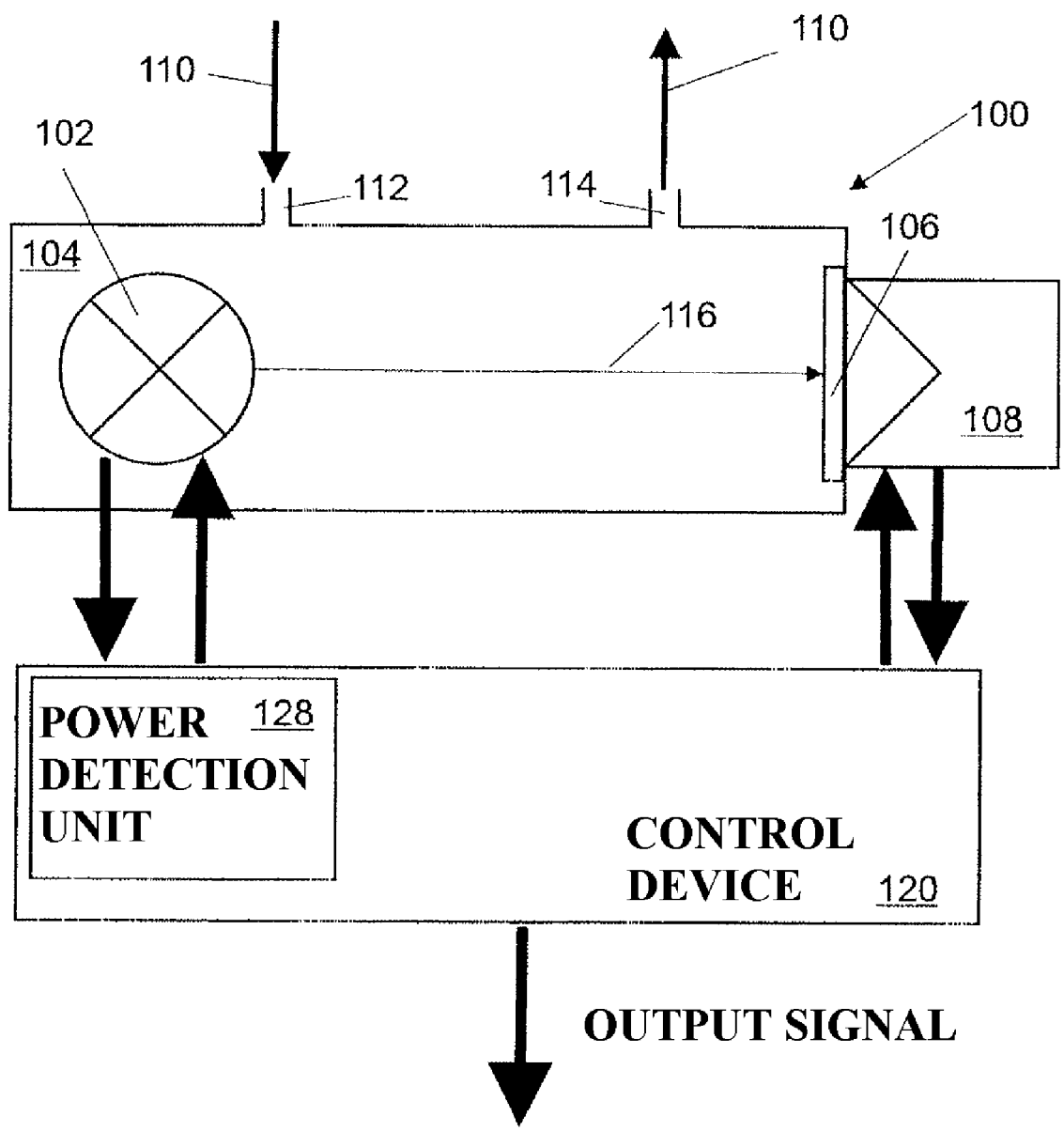
FIG. 1 is a block circuit diagram of a gas sensor arrangement according to the invention.

The construction and operation of the gas sensor arrangement according to the invention will be described in more detail in the following description with reference to the figures. As shown in FIG. 1, the gas sensor arrangement 100 according to the invention comprises a radiation source 102, in this case a broadband infrared radiation source. In principle, the gas sensor arrangement 100 which is illustrated is a so-called NDIR (non-dispersive infrared) sensor. In addition to the broadband infrared radiation source 102, which, in the simplest case, is formed by an incandescent lamp, the fundamental components are a gas measuring chamber 104, a filter 106 and an infrared detector 108.

The gaseous analyte 110 is pumped or diffused into the gas measuring chamber 104, symbolized in FIG. 1 by the inlet 112 and the outlet 114, in order to be measured. The gas concentration may be determined electro-optically via the absorption of a specific wavelength in the infrared range. If carbon dioxide is detected, the characteristic wavelength is 4.25 μm. In this process, the emitted infrared radiation 116 is guided through the gas measuring chamber 104 to the detector 108. The detector 108 has a filter 106 which passes only the wavelength range in which the gas molecules to be detected absorb. Other gas molecules do not usually absorb light in this wavelength and thus do not influence the amount of radiation which arrives at the detector 108. The infrared signal is usually chopped or modulated by the radiation source in order to be able to filter thermal background signals out of the desired signal. A control device 120 on the one hand triggers the radiation source 102 and on the other hand receives the output signals from the detector 108 and further processes them.

The present invention is based on the recognition that the internal resistance of the radiation source 102, in this case, an incandescent lamp, changes as the service life increases. This means that the change in the age-induced lamp brightness in conventional types of operation (i.e. constant voltage or constant current) is caused by different electric outputs being converted into radiation. Thus, according to the invention, the electrical output which is converted in each case in the radiation source 102 is measured in the control device 120 by a power detection unit 128. In this way, the electrical energy converted by the radiation source 102 during the measurement may be determined.

The power detection unit 128 may determine the electrical output of the radiation source 102 and, detected over the entire measuring time, the working integral of the radiation source 102 during the measurement. This value is used according to the invention in the control device 120 as a correction factor for standardizing to a source brightness, which prevailed at the time of the calibration initially carried out in the manufacturing calibration site.

Based on the correction factor, the control device 120 may influence the triggering of the radiation source 102 and adapt the radiation source brightness for the subsequent measurement. Alternatively or additionally, the control device 120 may adapt the sensitivity of the detector 108. Finally, during the evaluation by the control device 120, the output signal may be adapted as a function of the electrical energy actually converted in the radiation source 102 and determined by the power detection unit 128. For this purpose, the control device 120 comprises a microcontroller which may be programmed accordingly.

Figure 2:
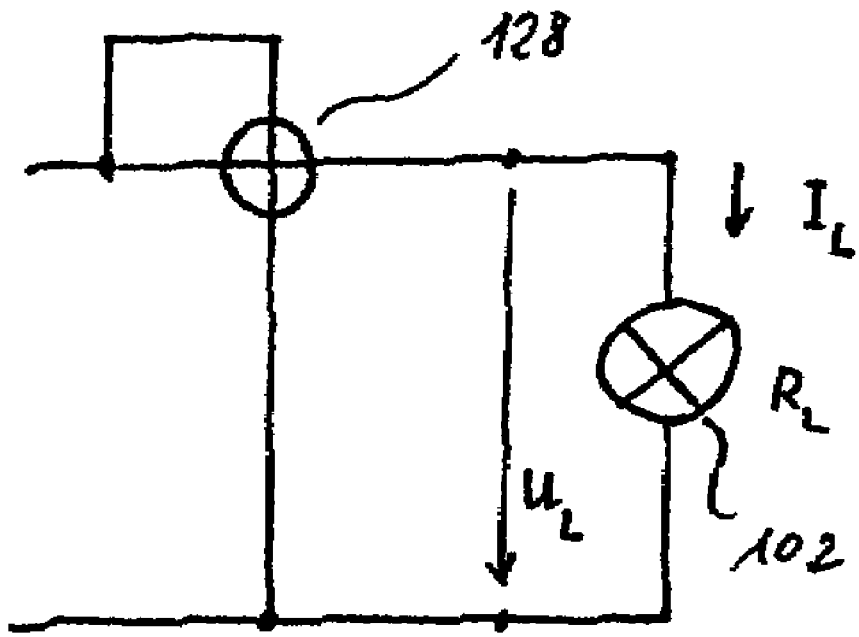
FIG. 2 is a simplified electric circuit diagram of the radiation source circuit according to a first possible embodiment.
Figure 3:
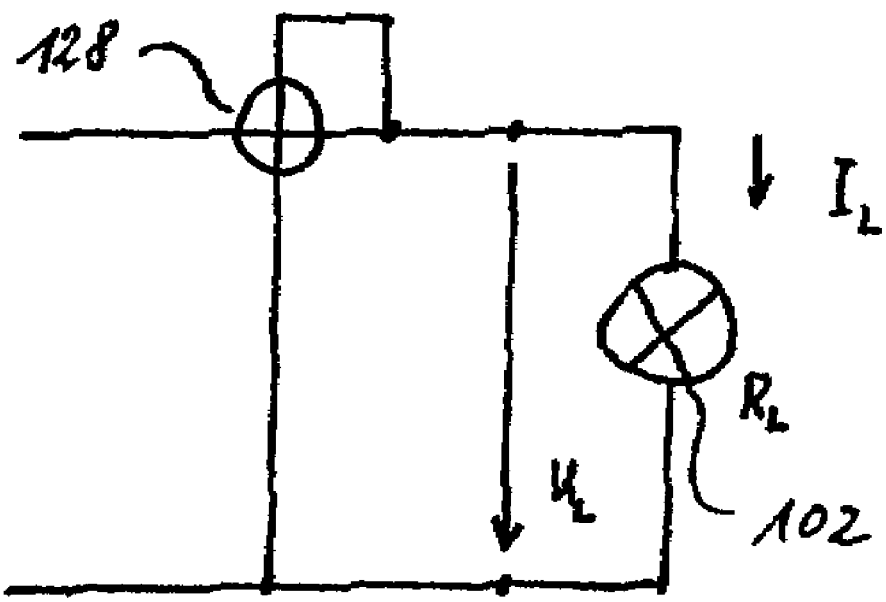
FIG. 3 is an electric circuit diagram of the radiation source circuit according to another embodiment.

As shown in FIGS. 2 and 3, the electrical output actually consumed by the radiation source 102 is detected, for example by a power detection unit 128 such as a multiplier, as is generally known to a person skilled in the art. In this case, as shown in both FIGS. 2 and FIG. 3 a wattmeter is used for the power detection unit 128, although it is also possible to use other multiplication methods, such as a Hall generator or a thermal wattmeter or it is possible to utilize the logarithmic connection between voltage drop and on-state current of a silicon diode path to measure the electrical output. In the circuit shown in FIG. 2, the same current flows through the power detection unit 128 as through the radiation source 102. In contrast thereto, the voltage lying at the power detection unit 128 is greater than the voltage at the radiation source 102 because of the voltage drop in the current path of the power detection unit 128. Seen from the radiation source 102, the consumer, the circuit of FIG. 2 is thus "current correct". Analogously, the arrangement shown in FIG. 3 is "voltage correct".

Figure 4:
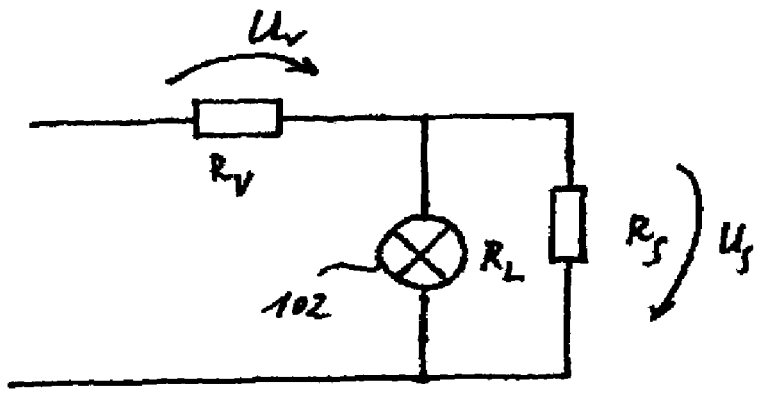
FIG. 4 is an electric circuit diagram of the power detection circuit according to another embodiment.

The electrical power converted in the radiation source 102 may, however, also be determined by a separate measurement of the current and voltage. FIG. 4 shows a circuit arrangement in which the radiation source 102 is operated via a series resistor $R_V$ and a shunt resistor $R_S$ connected in parallel to the radiation source 102. These resistors are constant and long-term stable and the voltages $U_V$ and $U_S$ dropping at the resistors may be measured by a conventional method for voltage measurement, for example using an A to D converter. This solution has the advantage that unused A to D converters are frequently available in the microcontrollers used for the control and may be used for measuring $U_V$ and $U_S$. The digital signal determined by the A to D converters may be directly further processed in the control device 120.

Figure 5:
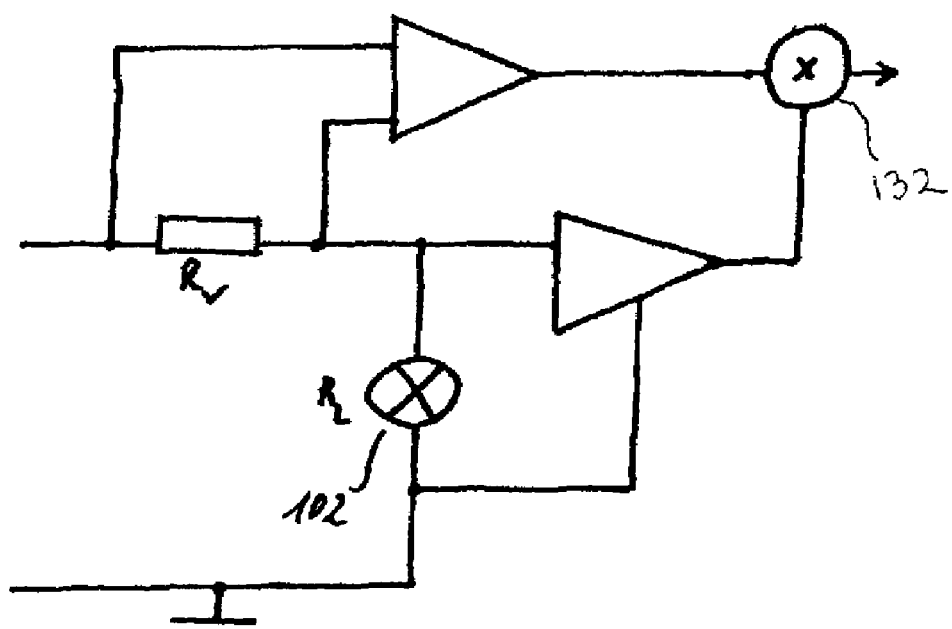
FIG. 5 is an electric circuit diagram of a power detection circuit at the radiation source circuit according to another embodiment.

FIG. 5 shows a circuit in which only one series resistor $R_V$ is used and the internal resistance $R_L$ of the radiation source 102 is directly used for measuring the power. In this case, the voltage is increased at the series resistor $R_V$ and the voltage is increased at the resistor $R_L$ of the radiation source 102 and supplied to a multiplier 132. The output signal of the multiplier contains the information concerning the electrical output consumed by the radiation source 102.

Figure 6:
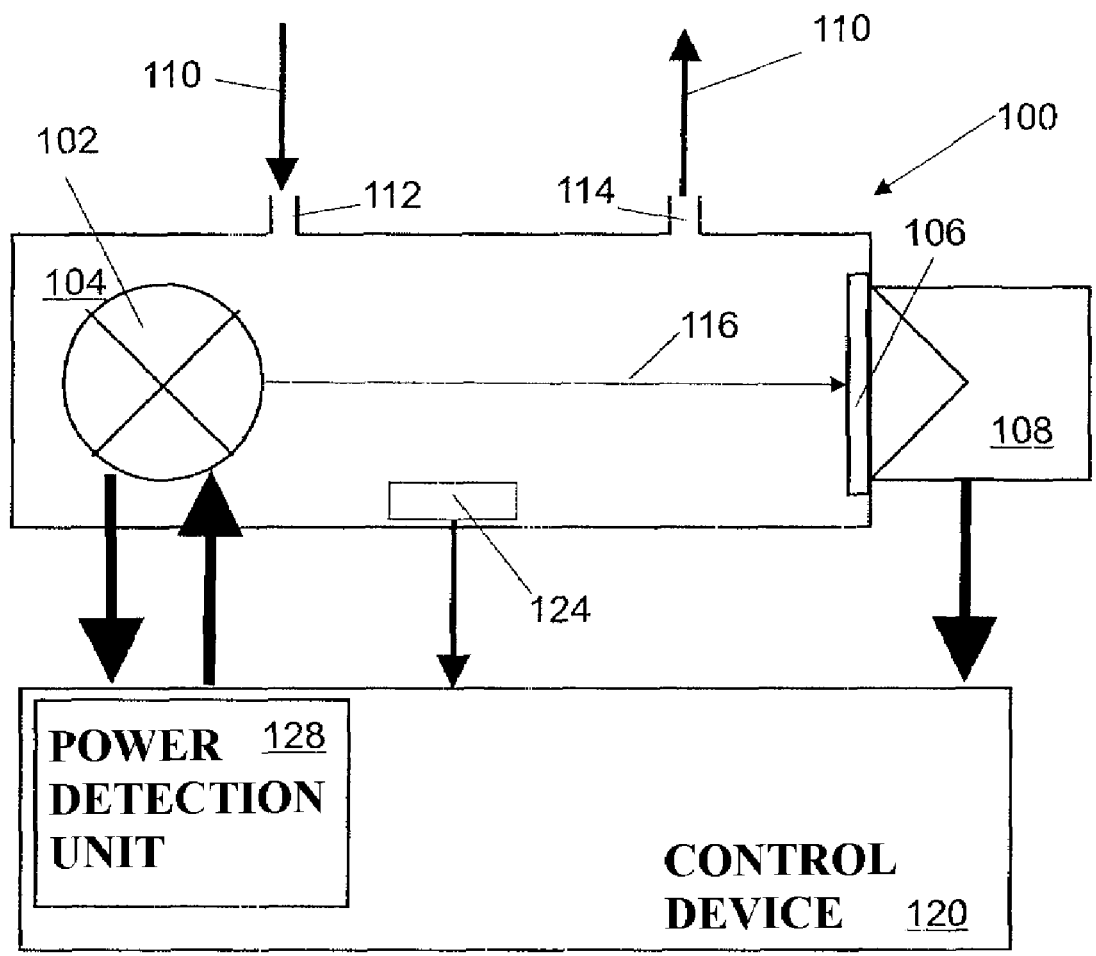
FIG. 6 is a block circuit diagram of a gas sensor arrangement with integrated temperature detection.

As shown in FIG. 6, the gas sensor arrangement 100 may also comprise at least one temperature sensor 124. The temperature sensor 124 detects the temperature in the gas measuring chamber 104 and outputs the information to the control device 120. In this way, further correction calculations may be carried out, for example on the detector signal and thereby the accuracy of the measurement may again be increased.

Figure 7:
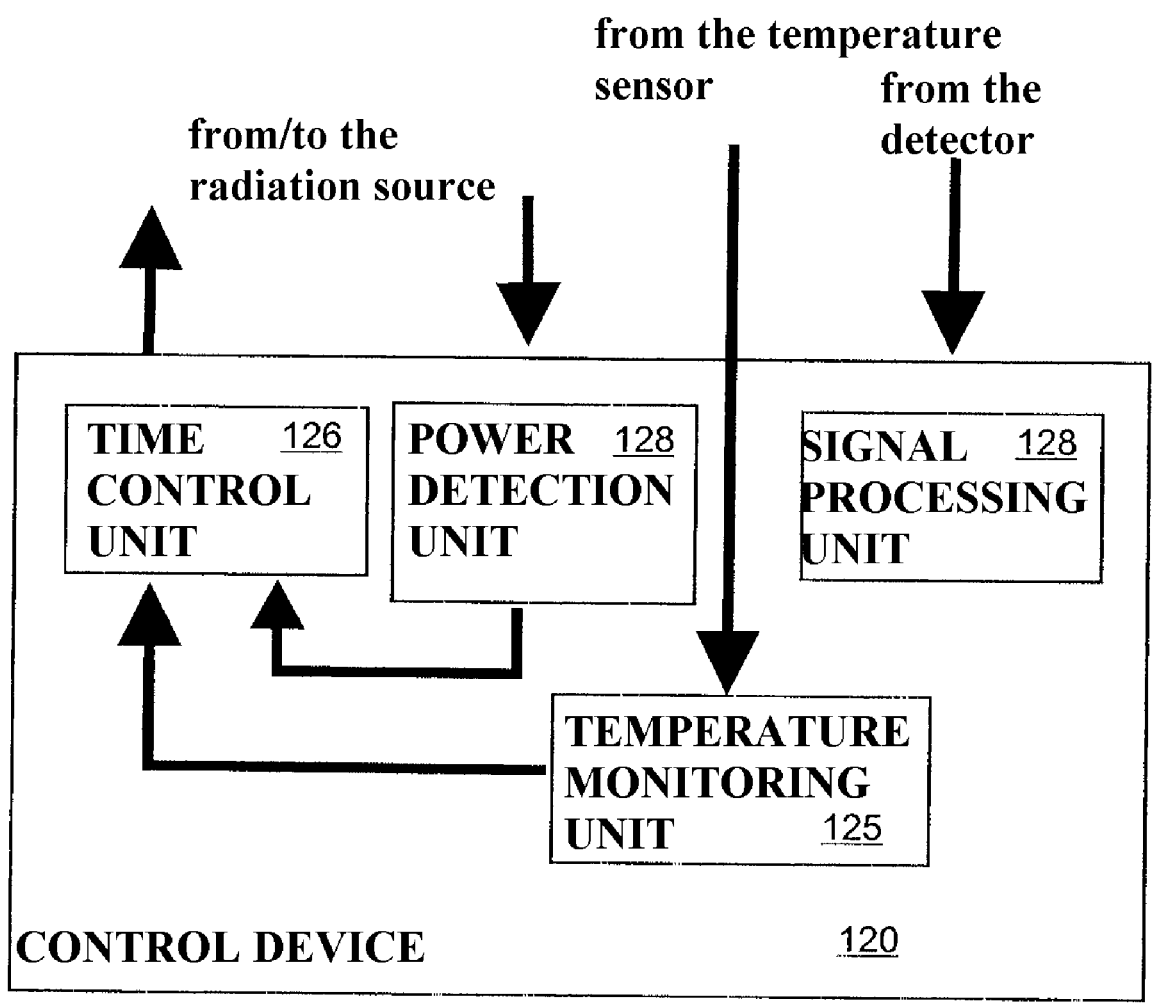
FIG. 7 is a block circuit diagram of the control device of FIG. 6.

As shown in FIG. 7, the control device 120 comprises a time control device 126 which, based on the power detection unit 128 and the optional temperature monitoring unit 125, triggers the radiation source 102 accordingly. This may be accomplished by using the principles of pulsed radiation emission as shown, for example, in German patent applications DE 10 2004 030855.1 and DE 10 2004 028077.0.

Figure 8:
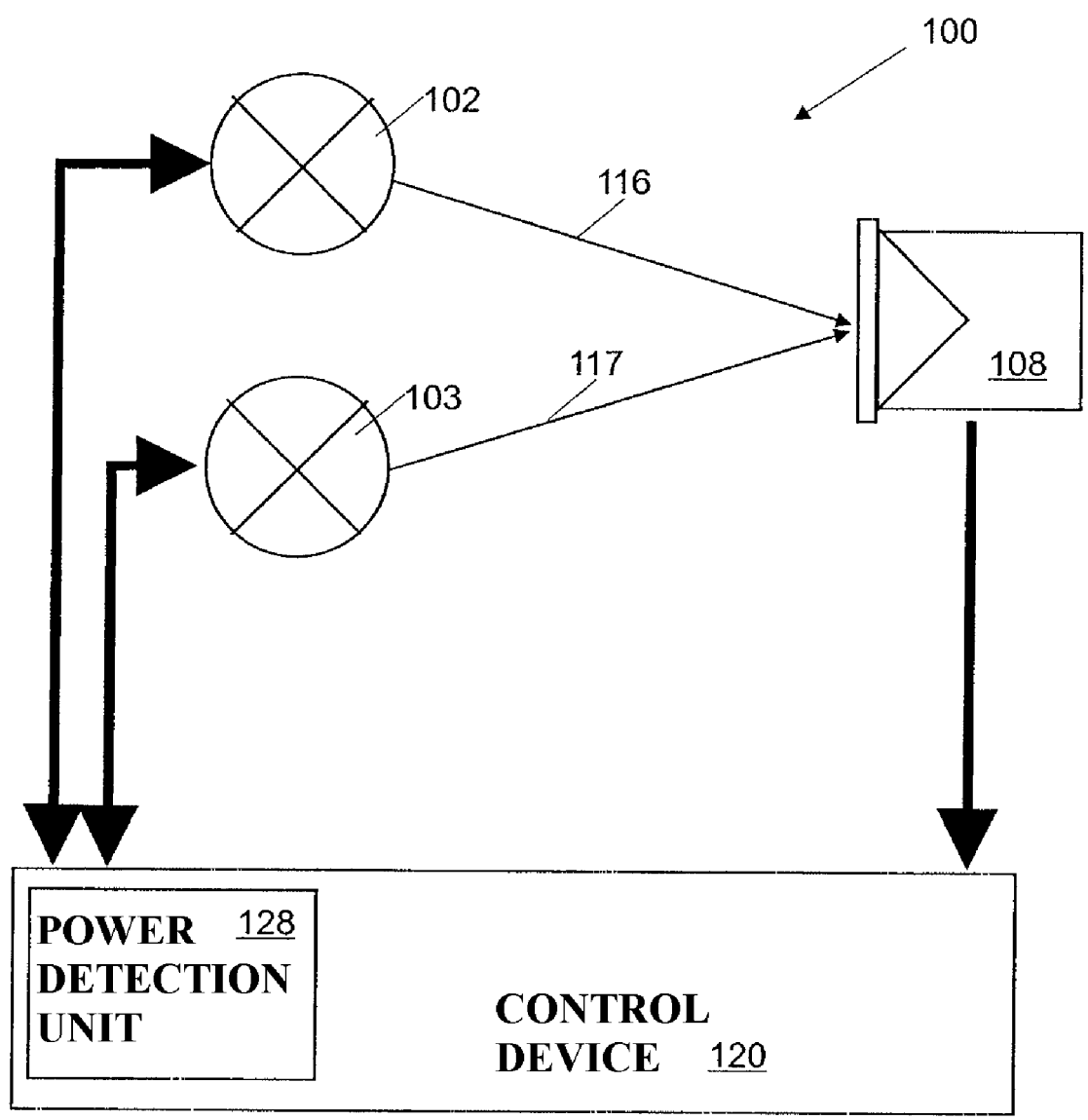
FIG. 8 is a block circuit diagram of a gas sensor arrangement with a measuring channel and a reference channel.

Due to the use of the power detection unit 128 according to the invention, it is possible to omit, during referencing, the second reference measuring channel shown, for example, in DE 19925196 C2, together with all the problems thereof, such as cost and requirements in terms of symmetry and constant ambient conditions. However, even if two channels are used which each have a separate radiation source 102, 103, the power detection according to the invention still provides an improvement in the accuracy of the system. FIG. 8 shows an arrangement of this type, in which the control device 120 on the one hand triggers the two radiation sources 102, 103, while the power input of the radiation sources is on the other hand monitored by the power detection unit 128.

Measurements have shown that the referencing without an additional power detection unit is problematic if the ambient conditions, such as temperature, pressure or gas concentration change during the referencing time. This is particularly critical if the gas sensor arrangement is positioned in the vicinity of air outlets of air-conditioning systems, open windows or poorly controlled heat sources. In these cases, the problem occurs that the reference measurements exhibit too great an error. Such errors may be clearly reduced using the embodiment shown in FIG. 8 which takes into account the respective power consumption of the radiation sources 102, 103, as a function of the measuring conditions.

The invention has the advantage that it is applied directly to the physical cause of the radiation intensity varying in the course of time, namely to the varying internal resistance of the radiation source. The possibilities of highly sensitive electrical measurements directly in the radiation source circuit make it possible to dispense with the defective measuring principles based on the detector signal. It is no longer necessary to reference with a second measuring channel or in particular to provide a second radiation source and/or another detector.

Advantageous embodiments may use the information about the consumed electrical output either for a controlling the radiation source brightness for the subsequent measurements or else for adapting the sensitivity of the detector to the currently prevailing radiation source brightness. Alternatively, even where the conditions for the radiation emission and radiation detection are unchanged, the results to be output may be corrected calculatively. The last variant in particular, in which adaptation in the triggering of the radiation source or of the detector is unnecessary, represents a particularly simple implementation possibility. In any case, the solution according to the invention can ensure that the requirements of measuring accuracy will be met even if the gas sensor arrangement is in use for more than ten years.

The advantageous principles of the present invention are effective particularly when the principle according to the invention is used for triggering a non-dispersive infrared lamp to measure $CO_2$. However, the principles according to the invention may of course also be applied to the use of other radiation sources and to analyze other gases, provided that the change in the long-term characteristics of the radiation source is associated with a change in the electrical internal resistance or a change in the electric output supplied with constant voltage or constant current.

In any case, the advantage of the solution according to the invention lies particularly in the fact that an electric characteristic variable which may be directly detected at the radiation source may be used for the radiation characteristic, which varies during the service life, of the radiation source and it is possible to dispense with the detector signal as an indicator of the ageing of the radiation source.

According to another advantageous embodiment, the gas sensor arrangement may, however, also comprise a measuring radiation source and an additional reference radiation source, the reference radiation source emitting radiation only to determine reference values. It has been shown that the referencing according to DE 19925196 C2 only functions in a disturbance-free manner when the ambient conditions, such as temperature, pressure or gas concentration, remain constant during the referencing time. However, if the sensors are used in the vicinity of air outlets of air-conditioning systems, open windows or poorly controlled heat sources, the problem occurs that the referencing procedures may only be carried out very rarely or with a lot of errors. According to the invention, a substantially higher accuracy may be achieved by measuring the actually converted electric output at both radiation sources.

What is claimed is:

1. A gas sensor arrangement comprising:
   at least one radiation source emitting radiation;
   a gas measuring chamber which may be filled with a gaseous analyte containing at least one analyte to be measured;
   at least one detector which detects the radiation and generates an output signal indicating the presence and/or the concentration of the analyte, and
   a control device for triggering the radiation source, wherein the control device comprises a power detection unit which may be operated in order to measure the electrical output consumed by the at least one radiation source.

2. The gas sensor arrangement according to claim 1, wherein the control device may be operated in order to adapt the triggering of the radiation source as a function of the measured electrical output.

3. The gas sensor arrangement according to claim 2, wherein the control device may be operated in order to adapt the evaluation by the detector unit as a function of the measured electrical output.

4. The gas sensor arrangement according to claim 3, wherein the radiation to be detected is infrared radiation and the at least one radiation source is formed by a lamp emitting a broadband light spectrum.

5. The gas sensor arrangement according to claim 4, wherein the radiation source is operated via a series resistor and a shunt resistor and the power detection unit is adapted to determine the voltages dropping at the series resistor and at the shunt resistor.

6. The gas sensor arrangement according to claim 5, wherein a measuring radiation source and a reference radiation source are provided and the reference radiation source emits radiation only to determine reference values.

7. The gas sensor arrangement according to claim 6, wherein at least one temperature sensor is provided for monitoring the temperature in the gas measuring chamber.

8. The gas sensor arrangement according to claim 7 having the capability of detecting gaseous analytes, such as carbon dioxide, and/or to determine the concentration thereof.

9. A method for measuring the presence and/or the concentration of an analyte using a gas sensor arrangement comprising at least one radiation source emitting radiation, a gas measuring chamber which may be filled with a gaseous analyte containing at least one analyte to be measured, and comprising at least one detector which detects the radiation and generates an output signal indicating the presence and/or the concentration of the analyte, comprising the following steps:
    triggering the radiation source to emit radiation;
    detecting and evaluating the radiation impinging on the detector, and
    measuring the electrical output consumed by the radiation source while emitting radiation.

10. The method according to claim 9, wherein the power supplied to the radiation source is adapted in a subsequent measuring cycle as a function of the measured electrical output.

11. The method according to claim 10, wherein a sensitivity of the detector is adapted as a function of the measured electrical output.

12. The method of claim 9, wherein a control unit carries out a calculative correction of the signal output by the detector as a function of the measured electrical output.

13. The method according to claim 12, wherein the step of measuring the power comprises:
    detecting the voltage drop at a series resistor connected in series to the radiation source and detecting the voltage drop at a shunt resistor connected in parallel to the radiation source.

14. The method according to claim 13, wherein the emitting of radiation comprises:
    emitting infrared radiation using a lamp emitting a broadband light spectrum.

15. The method according to claim 14 wherein gaseous analytes, are detected and/or the concentration thereof is determined.

* * * * *